(12) United States Patent
Steinhardt

(10) Patent No.: US 8,764,827 B2
(45) Date of Patent: Jul. 1, 2014

(54) TEST DEVICE FOR HAVING THERMAL DUMMY FOR OSSICULAR PROSTHESIS WITH MEMORY EFFECT

(75) Inventor: Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 13/574,637

(22) PCT Filed: Feb. 16, 2011

(86) PCT No.: PCT/EP2011/000727
§ 371 (c)(1),
(2), (4) Date: Jul. 23, 2012

(87) PCT Pub. No.: WO2011/141072
PCT Pub. Date: Nov. 17, 2011

(65) Prior Publication Data
US 2012/0310346 A1 Dec. 6, 2012

(30) Foreign Application Priority Data
May 12, 2010 (DE) .......................... 10 2010 020 412

(51) Int. Cl.
*A61F 2/18* (2006.01)
*B65D 85/00* (2006.01)
*G09B 23/28* (2006.01)

(52) U.S. Cl.
USPC ................................ 623/10; 600/25; 434/267

(58) Field of Classification Search
USPC ........... 623/10; 607/55–57; 600/25; 434/267; 206/438; 269/265–270
See application file for complete search history.

(56) References Cited

U.S. PATENT DOCUMENTS

| | | | |
|---|---|---|---|
| 5,356,418 A * | 10/1994 | Shturman | 606/159 |
| 5,615,770 A | 4/1997 | Applebaum et al. | |
| 6,060,639 A * | 5/2000 | Petrick | 623/11.11 |
| 6,197,060 B1 * | 3/2001 | Knox | 623/10 |
| 6,554,861 B2 | 4/2003 | Knox et al. | |
| 6,579,317 B2 | 6/2003 | Kurz | |
| 7,603,788 B2 * | 10/2009 | Kurz et al. | 33/512 |
| 2007/0021833 A1 * | 1/2007 | aWengen et al. | 623/10 |
| 2009/0164010 A1 | 6/2009 | Steinhardt et al. | |

FOREIGN PATENT DOCUMENTS

| | | |
|---|---|---|
| DE | 10 2007 062 151 | 12/2008 |
| EP | 1 181 907 | 2/2002 |
| WO | 02/069850 | 9/2002 |

* cited by examiner

*Primary Examiner* — David Isabella
*Assistant Examiner* — Yashita Sharma
(74) *Attorney, Agent, or Firm* — Michael J. Striker

(57) ABSTRACT

A test device for an ossicular prosthesis for implantation in the middle ear that includes a first fastening element, a second fastening element and a connecting element that connects the two fastening elements in a sound-conducting manner. Parts of the ossicular prosthesis are made of a material having memory effect and subjected to shape-altering thermal treatment at implantation. The test device also includes a device for determining an optimized power setting or an energy application site for preparing parts of the ossicular prosthesis to be subjected intraoperatively to thermal treatment using a prosthesis mock-up that is identical in design to the ossicular prosthesis in terms of material, geometric shape, and manufacturing method in the parts to be subjected intraoperatively to thermal treatment.

19 Claims, 14 Drawing Sheets

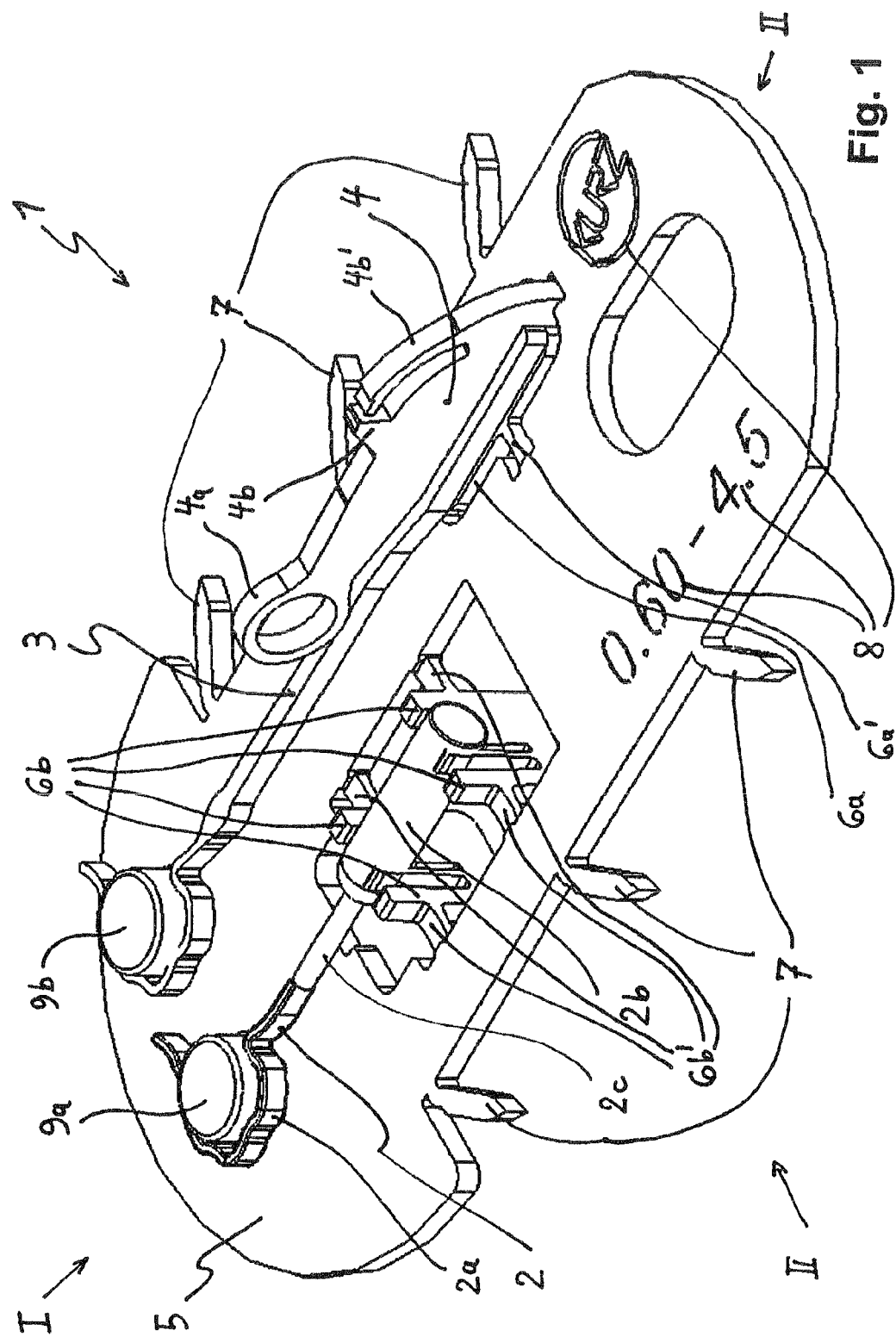

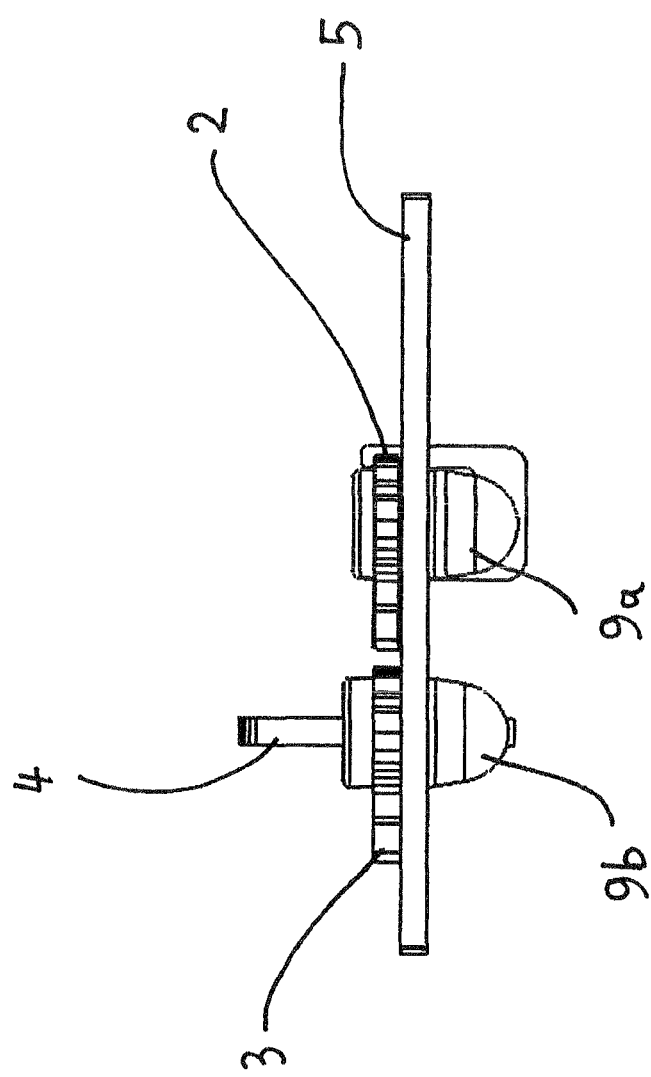

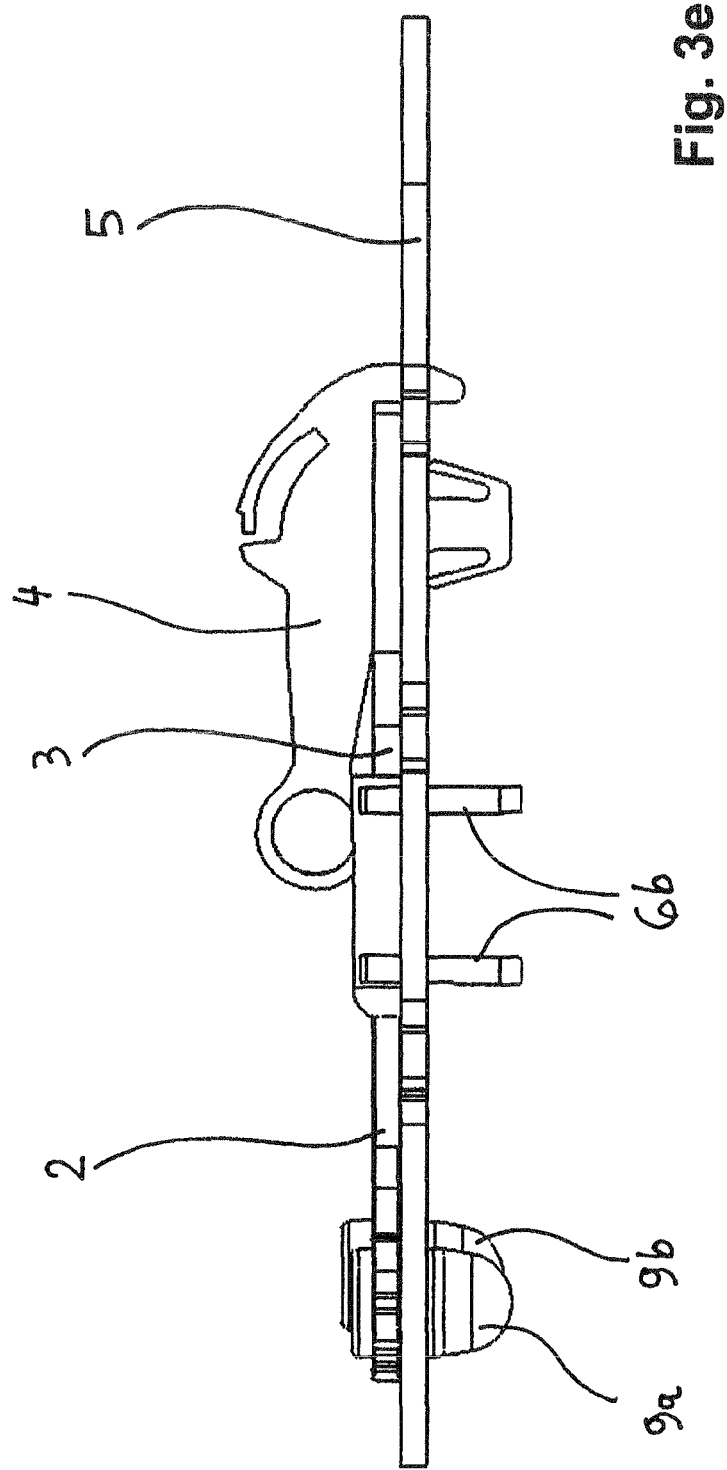

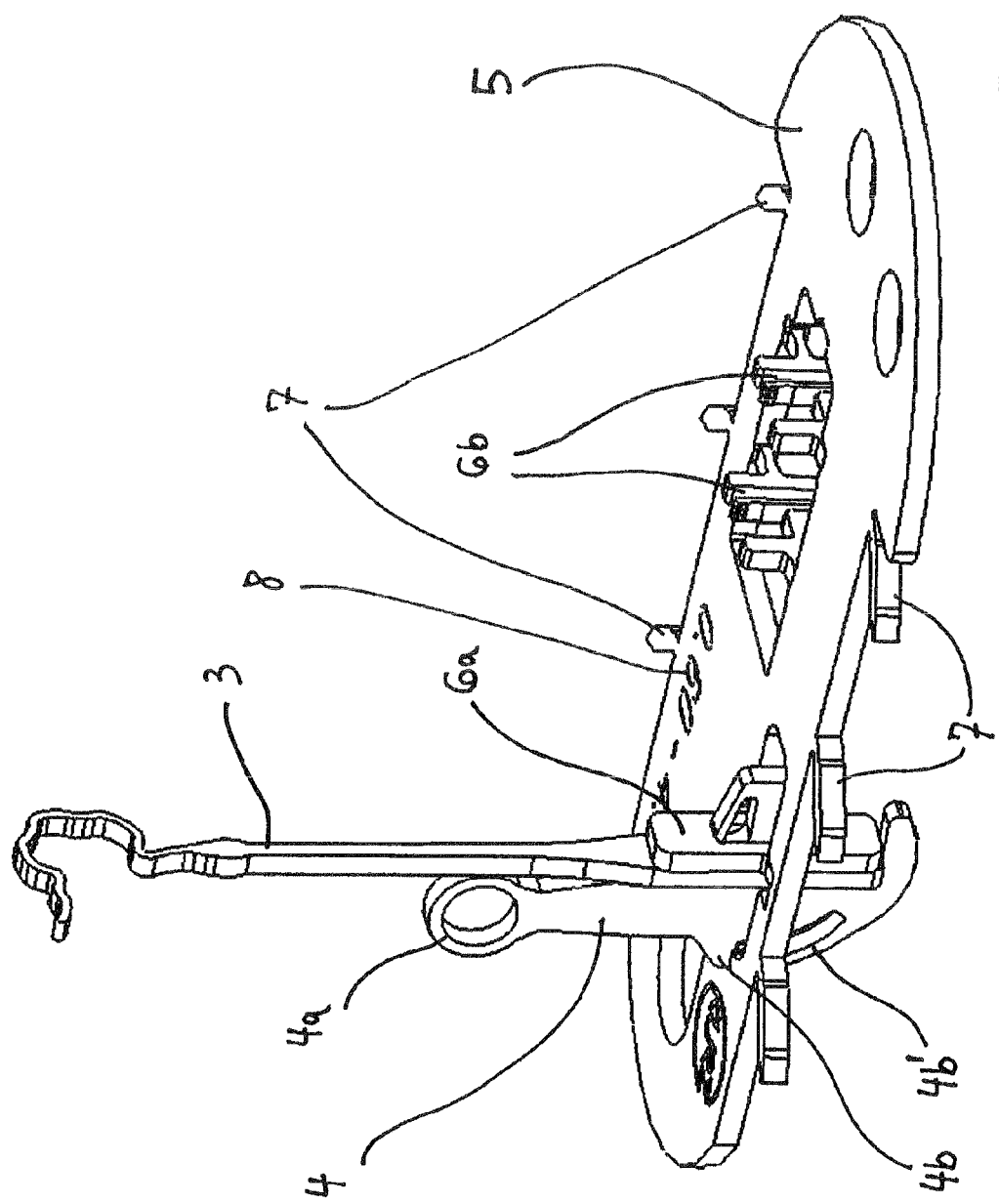

Figure 2A:
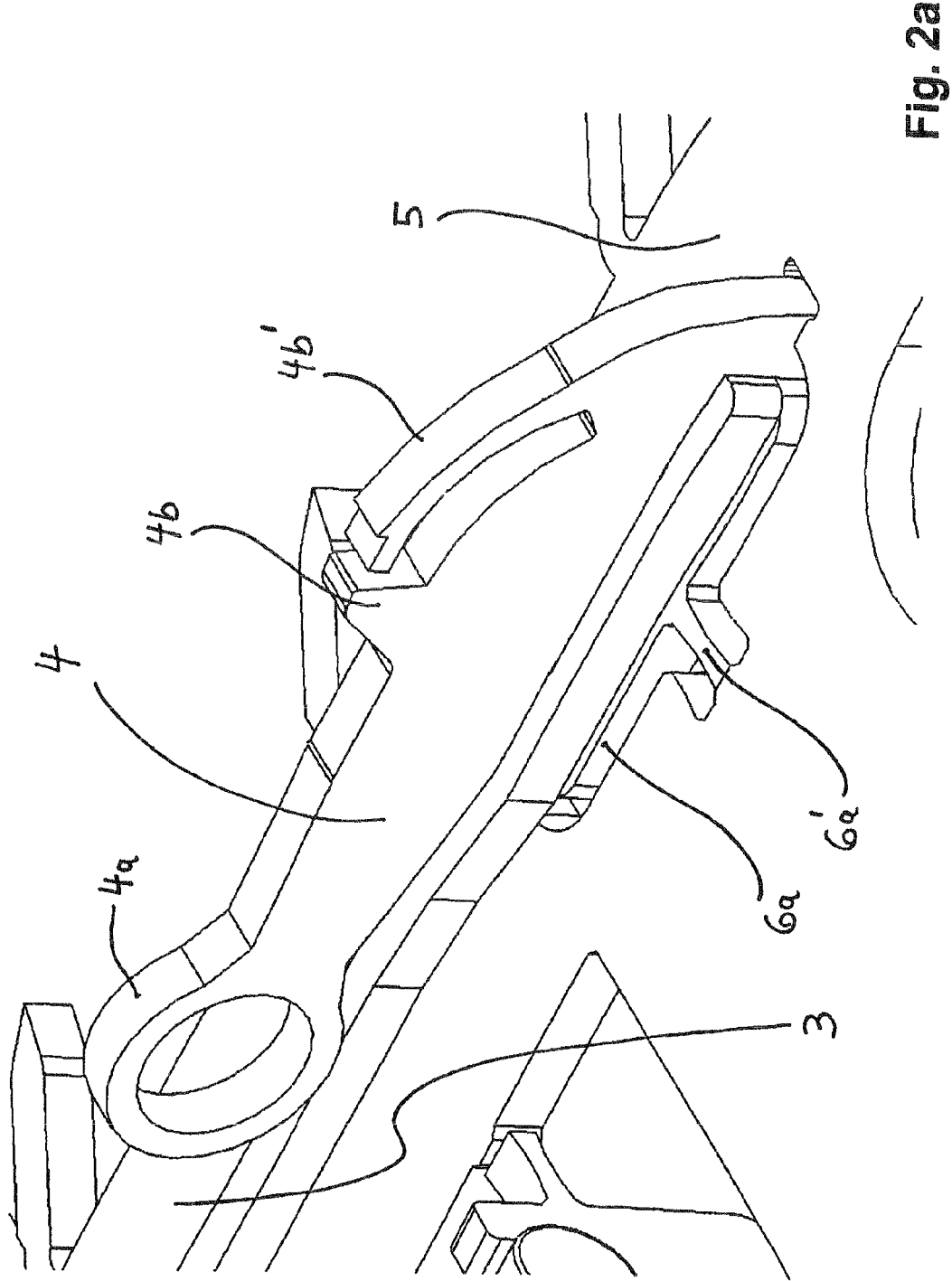

TEST DEVICE FOR HAVING THERMAL DUMMY FOR OSSICULAR PROSTHESIS WITH MEMORY EFFECT

CROSS-REFERENCE TO A RELATED APPLICATION

The invention described and claimed hereinbelow is also described in German patent Application 10 2010 020 412.9 filed on May 12, 2010. This German Patent Application, whose subject matter is incorporated here by reference, provides the basis for a claim of priority of invention under 35 U.S.C. 119 (a)-(d).

The invention relates to a test device comprising an ossicular prosthesis for implantation in the middle ear, which replaces or bridges at least one component or parts of a component of the human ossicular chain, wherein the ossicular prosthesis includes, at one end thereof, a first fastening element for mechanical connection to the tympanic membrane or a component of the ossicular chain, more particularly the limb of incus or the manubrium of malleus, and, at the other end thereof, includes a second fastening element for mechanical connection to a further component, or parts of a component, of the ossicular chain, or directly to the inner ear, and includes a connecting element that connects the two fastening elements in a sound-conducting manner, and wherein at least parts of the ossicular prosthesis are made of a material having memory effect and are subjected to shape-altering thermal treatment when the ossicular prosthesis is implanted in the middle ear. Ossicular prostheses of that type, in which at least one fastening element is made of Nitinol and is brought into the final shape thereof intraoperatively in the middle ear by way of thermal treatment, are known from WO 02/069850 A1 or U.S. Pat. No. 6,554,861 B2, for example.

Ossicular prostheses are used to conduct sound or the sound signal from the tympanic membrane to the inner ear in cases in which the ossicles of the human middle ear are missing or damaged, in entirety or in part. The ossicular prosthesis has two ends. Depending on the specific circumstances, one end of the ossicular prosthesis is fastened to the tympanic membrane, e.g. using a top plate, and the other end of the ossicular prosthesis is fastened, e.g. to the stapes of the human ossicular chain, or it is inserted directly into the inner ear.

Three types of ossicular prostheses that are used particularly frequently are stapes prostheses, partial prostheses, and total prostheses. Stapes prostheses are fixed to the incus, and extend via a piston into the inner ear. Partial prostheses typically bear via a top plate against the tympanic membrane and establish a connection to the head of the stapes. Total prostheses connect the tympanic membrane to the base of the stapes.

The ossicular prostheses of the type in question are also alike in that the fastening thereof to a component of the ossicular chain during implantation is brought about or at least supported in that the entire prosthesis, or at least the corresponding fastening element, was made of a material having memory effect, which was subjected preoperatively to deformation under defined temperature conditions. In order to now permanently attach a fastening element, which is designed as a loop, for example, the loop is initially placed relatively approximately around the miniscule subregion of the ossicle, is positioned exactly and is subsequently subjected to thermal treatment—usually using a laser or an electrical device—such that the specific deformation of the memory material results in a final closure of the loop around the ossicle, said closure becoming permanent at body temperature. An analogous procedure is used for fastening elements having other shapes.

In that particular case it is problematic, however, that the application of excessive luminous power or electrical energy has the undesired effect of excessive local heating and, therefore, generating a temperature that is too high in the region of the fastening element, which is transmitted to the ossicle and can quickly result in damage or even necrosis of the sensitive bodily tissue at the related section of the ossicle. The final result of the entire operation could then possibly even be counterproductive.

Of course the manufacturers of middle ear prostheses of the type in question typically make claims about optimal method parameters for the "preparation" of their prostheses having memory effect. However, due solely to the fact that the devices for thermal treatment employed on-site by the users can differ greatly, these claims can only cover ranges that are very wide and are therefore often of little informative value. In addition, it does little good to inform an operating surgeon about what local maximum temperature he must not exceed in the thermal treatment. He certainly knows that protein coagulates at temperatures starting at approximately 60° C. and can permanently damage bodily tissue. Thus he must find a suitable setting for the power output of the device he will use, and identify the point of energy application onto the ossicular prosthesis that is optimal for his purposes, before he performs the operation in the middle ear.

The problem addressed by the present invention is therefore that of providing a test device comprising a middle ear prosthesis of the initially described type in an uncomplicated and low-cost manner using the simplest possible technical means, which provides the operating surgeon with an uncomplicated way to determine a parameter setting—intraoperatively and shortly before the actual implantation of the middle ear prosthesis—that is optimal in terms of the thermal treatment devices available to him, without any need for the middle ear prosthesis itself to be touched and therefore possibly changed in any way, which is undesired.

This problem is solved according to the invention in a manner that is as surprisingly simple as it is effective in that the test device comprises a device for determining an optimized power setting and/or energy application site for preparing parts of the ossicular prosthesis to be subjected intraoperatively to thermal treatment, and in that said device contains a prosthesis mock-up which matches the ossicular prosthesis and, at least in the region in which the associated ossicular prosthesis will be subjected intraoperatively to thermal treatment, is identical to the ossicular prosthesis in terms of material, geometric shape, and manufacturing method.

In this manner, the operating surgeon can determine the optimal parameters for the thermal treatment to be performed in situ on the ossicular prosthesis in the middle ear in advance on the prosthesis mock-up using the devices available to him, and easily test out planned handling steps on the outside instead of in the middle ear, without any need to even touch the original prosthesis and thereby possibly cause deformation or deformation thereof. The parameters determined in this manner correspond very exactly to the parameters that apply for the original prosthesis, because the mock-up of the prosthesis is an identical match to the original prosthesis, at least at the points intended for thermal treatment.

One of the main problems that arises in every case of reconstructing the human ossicular chain involves selecting the correct length of prosthesis. The lengths that are required vary within a range of several millimeters, due to differences in anatomy. When an ossicular prosthesis is surgically implanted, it is therefore necessary to have on hand a sufficiently large selection of prostheses having different axial lengths, or it must be possible to reduce the maximum starting length of the ossicular prostheses to the final axial length that is required. Length-variable ossicular prostheses of that type are known in several different embodiments in the prior art.

In a preferred class of embodiments of the test device according to the invention, the ossicular prosthesis therefore comprises such a device for varying the length thereof, which is usually disposed in the region of the connecting element between the two ends of the prosthesis. The ossicular prosthesis and the associated prosthesis mock-up are then made of a material having memory effect, at least in the region of the device for varying the length.

Alternatively or in addition thereto, it is possible in further embodiments of the invention for the ossicular prosthesis and the associated prosthesis mock-up to be made of a material having memory effect, at least in the region of the particular first fastening element, to permit the optimal parameter for the above-described intraoperative closure of the fastening element to be determined preoperatively.

In a particularly simple class of embodiments of the test device according to the invention, the ossicular prosthesis and the associated prosthesis mock-up are designed entirely identical to one another in terms of material and geometric shape. Therefore, the operating surgeon only needs to have two identical middle ear prostheses at his disposal, one of which he can then use as the prosthesis mock-up, while he subsequently implants the other one in the middle ear.

A further considerable improvement of the handling is attained in embodiments in which the test device contains a detent device that can be used to fix the prosthesis mock-up at least in a processing position. The rigid and non-displaceable position of the prosthesis mock-up during determination of optimal parameters simplifies the work being performed and increases the quality of the parameters that are found.

Embodiments of the test device according to the invention that are particularly preferred and that are convenient for the user are characterized in that a holding device is provided that can accommodate the prosthesis mock-up in a swivellable manner. It is therefore possible to ensure that the prosthesis mock-up is positioned in a stable, easily accessible manner while the optimal treatment parameters are being determined, and that transport to the "application site" is gentle and damage-free.

Developments of the test device according to the invention are particularly comfortable to handle and easy to produce are those in which the holding device is formed as a plate made of thin metal sheet and comprises a suspending device, which is connected to the plate in a twistable manner, for suspension of one end of the prosthesis mock-up.

In terms of damage-free transport, developments of the above-described embodiments are also advantageous that are characterized in that the holding device comprises a device for ensuring safe transport, which has burr-shaped segments extending laterally from the holding device.

Developments of the above-described embodiments can further simplify the handling of the test device according to the invention when the holding device is designed such that it can also accommodate the ossicular prosthesis belonging to the prosthesis mock-up.

Developments are also particularly preferred in which the holding device optically coded and/or labelled, wherein the coding or labelling contains technical information regarding the ossicular prosthesis and/or the associated prosthesis mock-up and/or manufacturer's information, thereby eliminating the need to look up these important data in a manual or information sheet provided with the test device, since they are available directly during handling of the test device.

Embodiments of the test device according to the invention are also advantageous and, therefore, particularly preferred that are characterized in that the ossicular prosthesis and/or the associated prosthesis mock-up is optically coded and/or labelled, and in that the coding or labelling contains technical information regarding the ossicular prosthesis and/or the prosthesis mock-up.

In both cases, it is simplest in terms of production engineering for the coding and/or labelling to be created using laser treatment and/or anodizing.

Developments are of particular practical advantage in which the technical information of the coding and/or labelling contains a recommended starting value for the electrical power or luminous power that should be used within the scope of a test handling of the prosthesis mock-up at the beginning of the determination of optimized processing parameters for the parts of the ossicular prosthesis to be subjected intraoperatively to thermal treatment.

In practical application, embodiments of the test device according to the invention also prove to be effective in which at least parts of the ossicular prosthesis and the associated prosthesis mock-up are made of a nickel-titanium alloy, more particularly of Nitinol.

The ossicular prosthesis of the test device according to the invention can be designed as a passive prosthesis. Alternatively, in embodiments of the invention, however, the ossicular prosthesis can also be connected to an active vibration part of an active, partially implantable hearing aid. This also enables further hearing damage caused by the use of modern electronic devices to be prevented or at least ameliorated in terms of the effect thereof, wherein a physical connection of the ossicular prosthesis to the outside world by way of a coating described below does not cause problems, which would be due to an increased introduction of bacteria into the region of the middle ear, when the coating is designed to be antibacterial.

The prosthesis will be designed according to the particular defect to be eliminated or at least ameliorated in terms of the effect thereof on the patient by the use of the ossicular prosthesis contained in the test device according to the invention. In a few embodiments of the invention, the first fastening element will comprise a top plate designed to be placed against the tympanic membrane. In many embodiments, the prosthesis can be attached on one side, for example, to the limb of incus or to the stapes, or it may be inserted directly into the inner ear. In this context, an embodiment is advantageous in which the ossicular prosthesis is located at the end of the hammer (=umbo) or directly adjacent thereto, thereby resulting in the greatest leverage for the mechanical transmission of sound via motions that occur in the artificial or natural ossicular chain.

One class of embodiments of the ossicular prosthesis used with the test device is characterized in that the second fastening element is designed as a plate, a sleeve, a loop, a closed bell, a bell having one or two slots, or as a clip for mechanical connection to a further component of the ossicular chain.

In developments of these embodiments, the prosthesis is fastened on one side via a top plate to the tympanic membrane and, on the other side, via the second fastening element to the incus or stapes.

Alternative embodiments may provide that the ossicular prosthesis is coupled via the end thereof to which the second fastening element is attached via perforation of the stapes (stapedectomy or stapedotomy), and/or by opening up the human cochlea (=cochleotomy), to which the top plate is attached at the opposite end, directly to the inner ear, using a plunger, in particular.

Once the prosthesis has been surgically implanted in the middle ear and the tympanic membrane has been closed, the recovery phase begins. Scars form during this period, and they produce unforeseeable forces which can cause the prosthesis to move out of localized position thereof. When there is a stiff connection between a top plate and the connecting element, increased pressure peaks may result between the edge of the top plate and the tympanic membrane, or the graft between the tympanic membrane and the top plate. These pressure peaks can be so high that penetration or extrusion through the tympanic membrane would result. For this reason, it is very helpful for the prosthesis to have a certain amount of post-surgical mobility, so that the top plate may automatically adapt, post-operatively, to the position of the tympanic membrane. Since, in addition, the unique anatomical features of the ear, such as the position, shape and size of the stapes, incus, hammer and tympanic membrane vary, it is very advantageous when ossicular prostheses are not designed to be rigid, but rather that they have a certain amount of flexibility or variability.

In the case of the ossicular prosthesis, the connecting element between the two fastening elements is typically designed as an elongated shank, as is well known from the related art. To attain the increased flexibility and variability of the prosthesis described above, it is possible according to a particularly preferred embodiment of the present invention, and as described extensively in EP 1 181 907 B1, for example, for at least one ball joint to be provided in the elongated connecting element. In terms of particularly high post-operative mobility of the prosthesis, developments are particularly advantageous in which the elongated shank includes a large number of further rotary elements that abut each other, preferably in the form of a ball joint chain.

Parts of the ossicular prosthesis and the associated prosthesis mock-up in the test device according to the invention can be made of titanium and/or gold and/or tantalum and/or steel, and/or an alloy of said metals. It is known that titanium, in particular, in addition to being stiff and having excellent sound-conducting properties, also exhibits excellent biocompatibility with the human ear.

In terms of the post-operative position adjustment mentioned above, embodiments of the invention are advantageous in which the prosthesis or parts thereof—in particular one of the fastening elements—are made of a material having superelastic properties, preferably Nitinol in particular, as is known per se from the initially cited document WO 02/069850 A1 or from U.S. Pat. No. 6,554,861 B2.

As an alternative or in addition thereto, in further embodiments, parts of the ossicular prosthesis according to the present invention may be composed of a ceramic material.

In addition to the post-operative shifting of position, a further problem results once ossicular prostheses have been implanted: The middle ear of the human body may be described as a "semi-open region". Any implantation material that is inserted in the body within the scope of reconstruction of the middle ear and its structures thereby undergoes a particular stress that predominates in a contaminated and infected environment, and which typically attacks the material. Since the objective of implanting an ossicular prosthesis must always be to enable the implant to remain in the patient's middle ear for as long as possible without complications occurring, a sustained attack on the material may result in damage being done to the prosthesis and/or in a local infection. Neither of these consequences is tolerable. In a further particularly preferred embodiment of the present invention, to permanently prevent damage from occurring to the implantation material or the surrounding tissue, the surface of the ossicular prosthesis is coated entirely or at least in sections with a biologically active coating, in particular a growth-inhibiting and/or growth-promoting and/or antibacterial coating.

In the case of the ossicular prosthesis contained in the test device according to the present invention, a fastening element designed as a top plate should always have a growth-promoting coating, but a fastening element that leads directly into the inner ear, in the form of a piston, for example, should have a growth-inhibiting coating.

According to a particularly preferred embodiment, the mass distribution of the individual parts of the prosthesis is calculated depending on a desired, specified or specifiable frequency response of sound conduction in the middle ear. This allows the sound propagation properties to be mechanically tuned to a certain extent using a custom-made ossicular prosthesis without a great deal of additional technical complexity.

In special embodiments, a tuning effect of this type may be attained, e.g., by fastening at least one additional mass to a part of the ossicular chain or the prosthesis depending on a desired, specifiable frequency response of sound conduction in the middle ear. In, advantageous developments of these embodiments, the additional mass is fastened to a part of the ossicular chain or the prosthesis using a clip. The additional mass and/or clip may also be coated with a biologically active coating.

Further features and advantages of the invention will become apparent from the detailed description of embodiments of the invention presented below with reference to the figures in the drawing which shows the details that are essential to the invention. Further features and advantages of the invention will also become apparent from the claims. The individual features may be implemented individually, or they may be combined in any possible manner to form variants of the invention.

Embodiments of the invention are depicted in the schematic drawing and are described in greater detail in the description that follows.

Figure 2B:
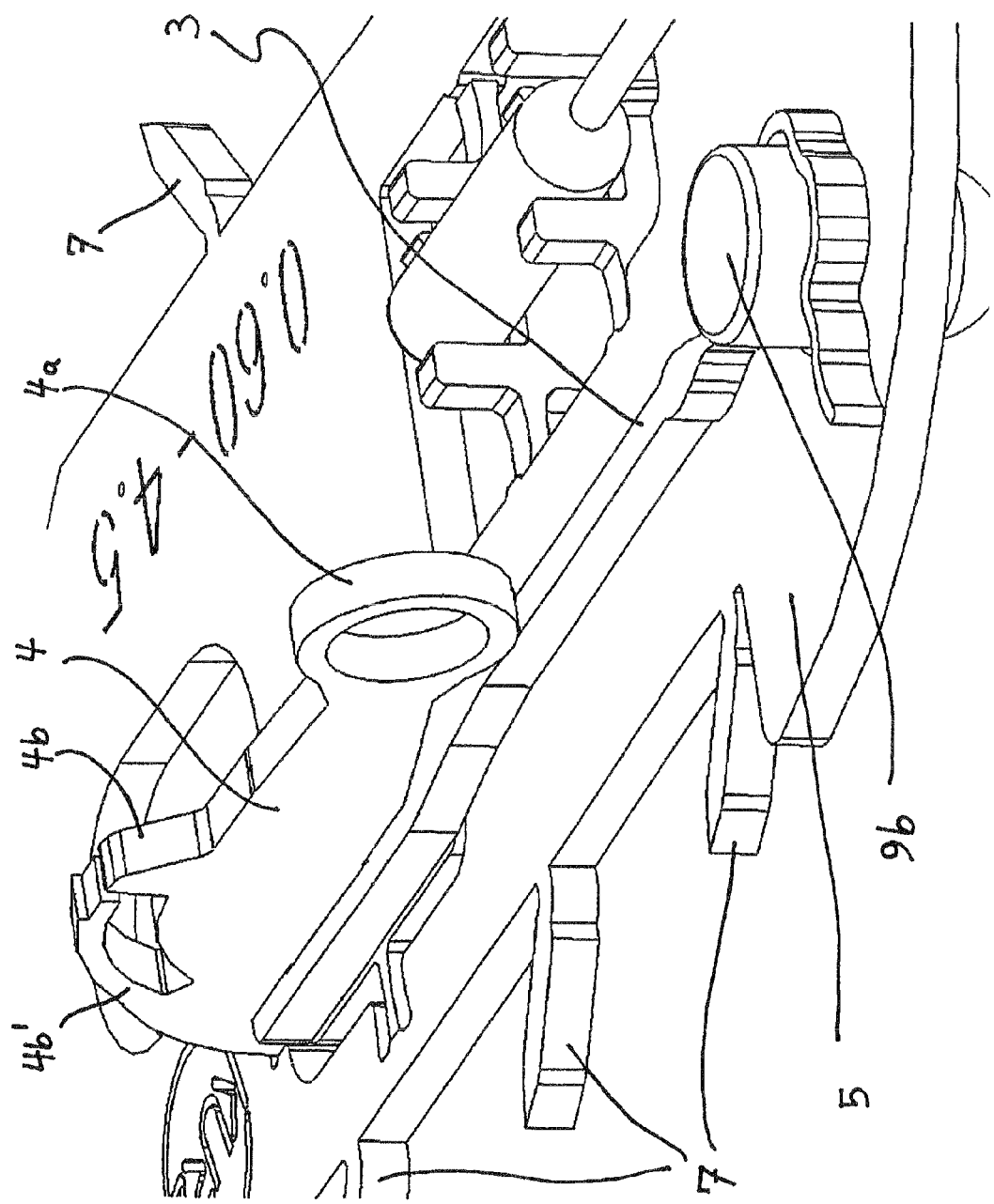
Figure 3A:
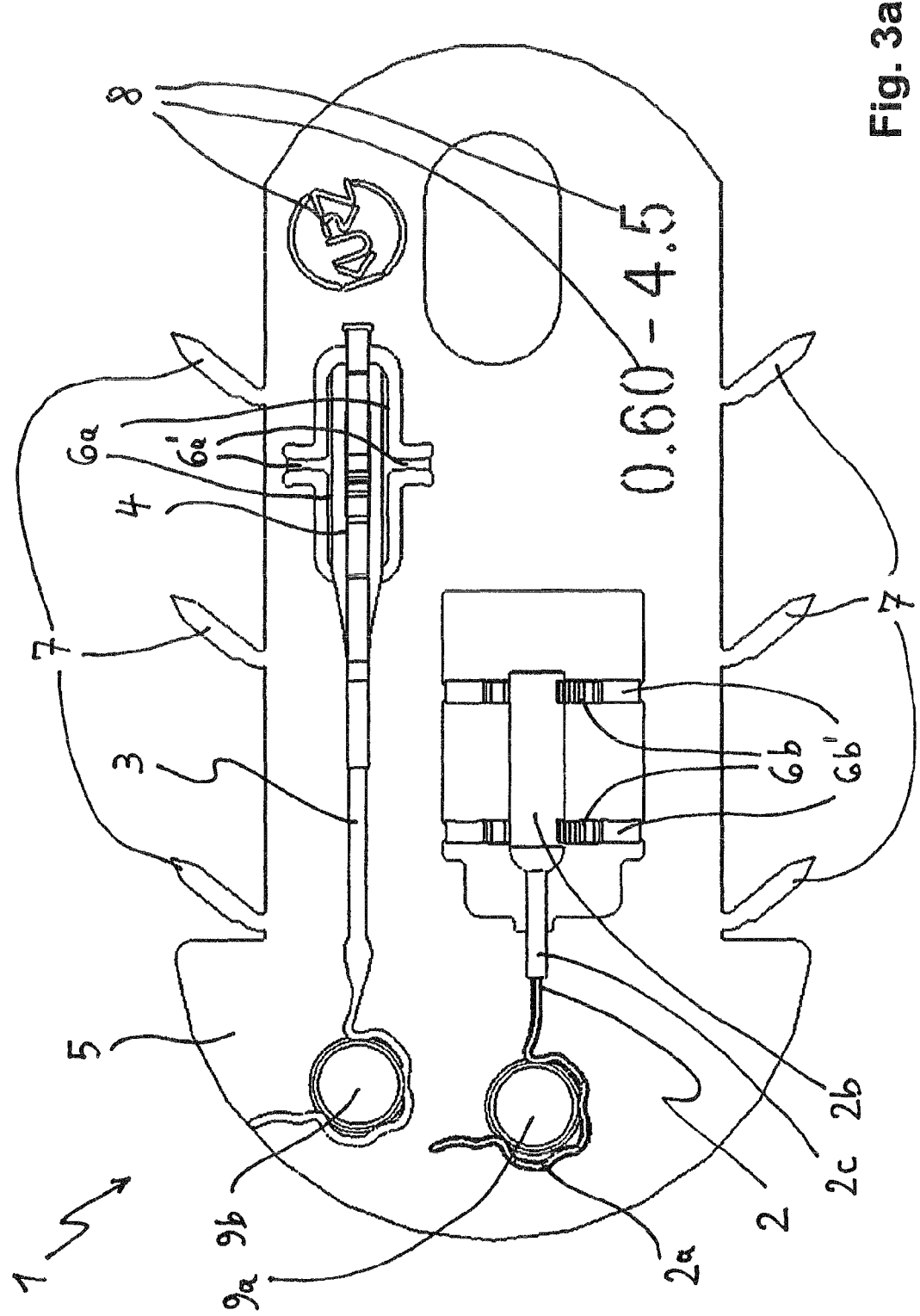
Figure 3B:
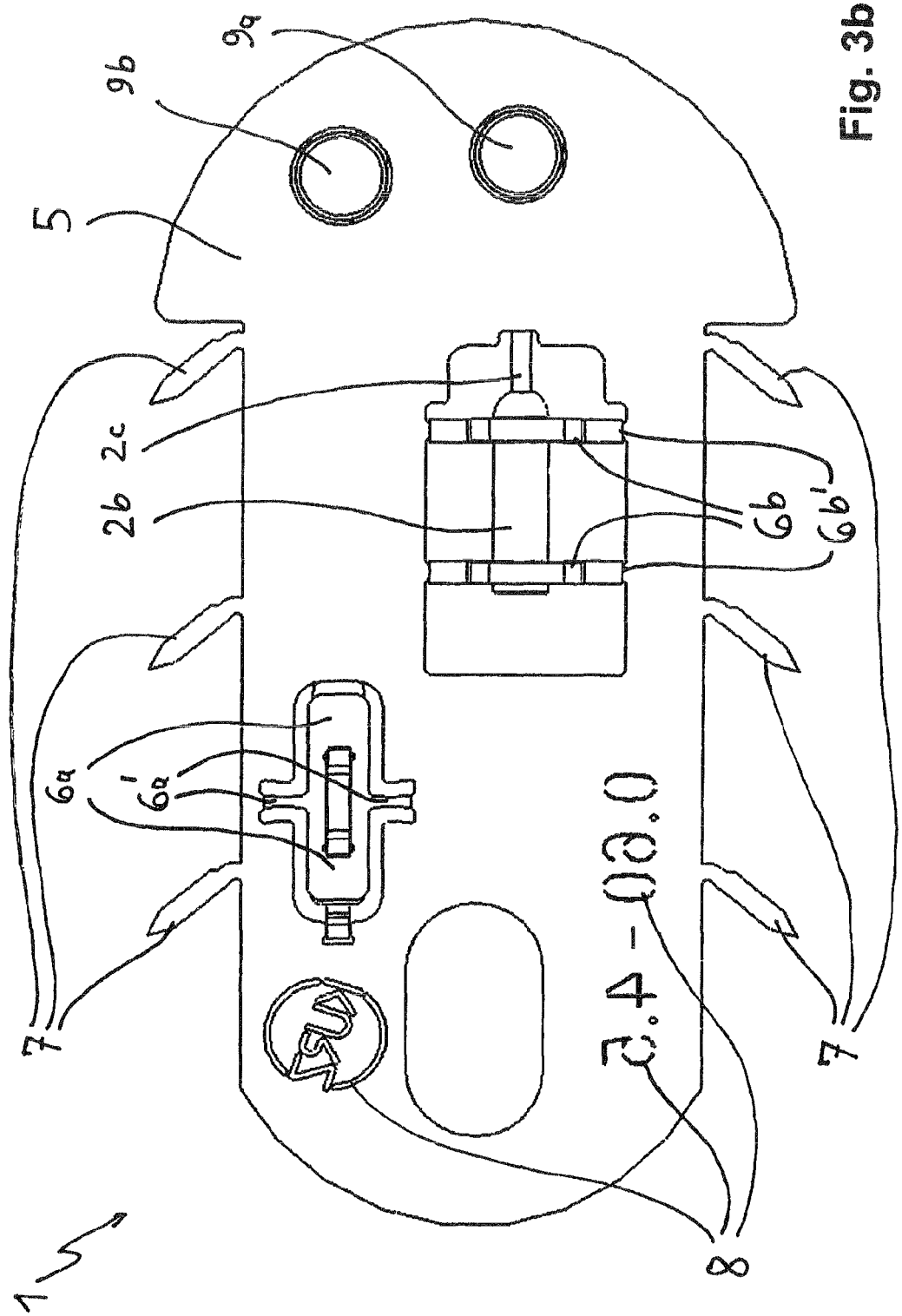
Figure 3D:
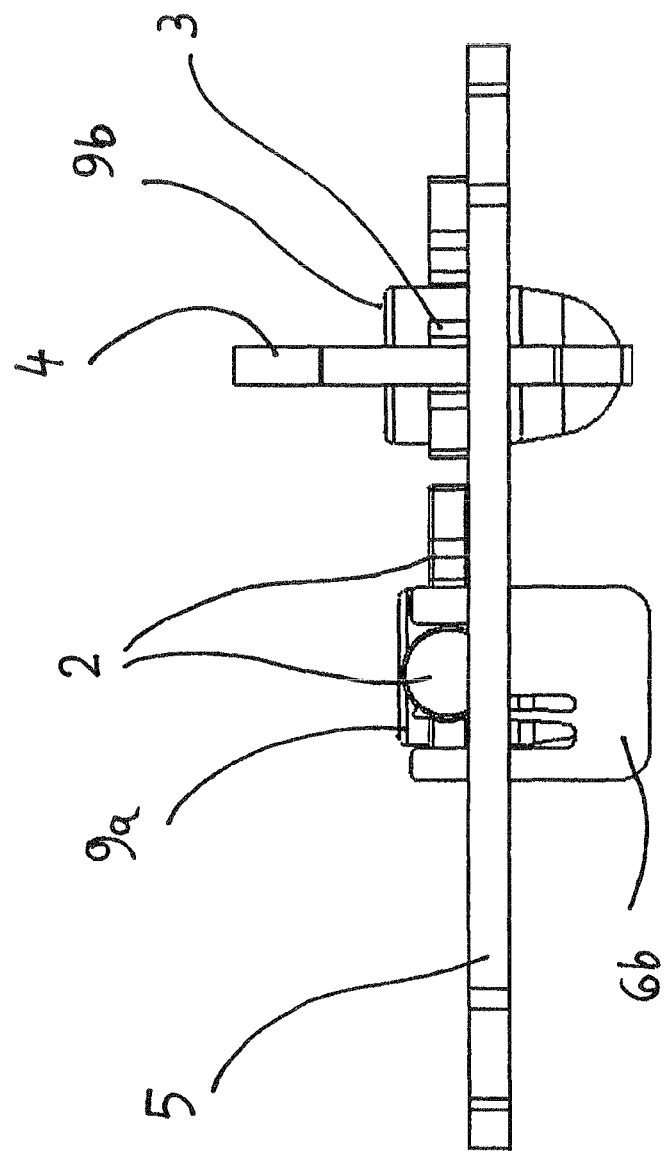
Figure 4A:
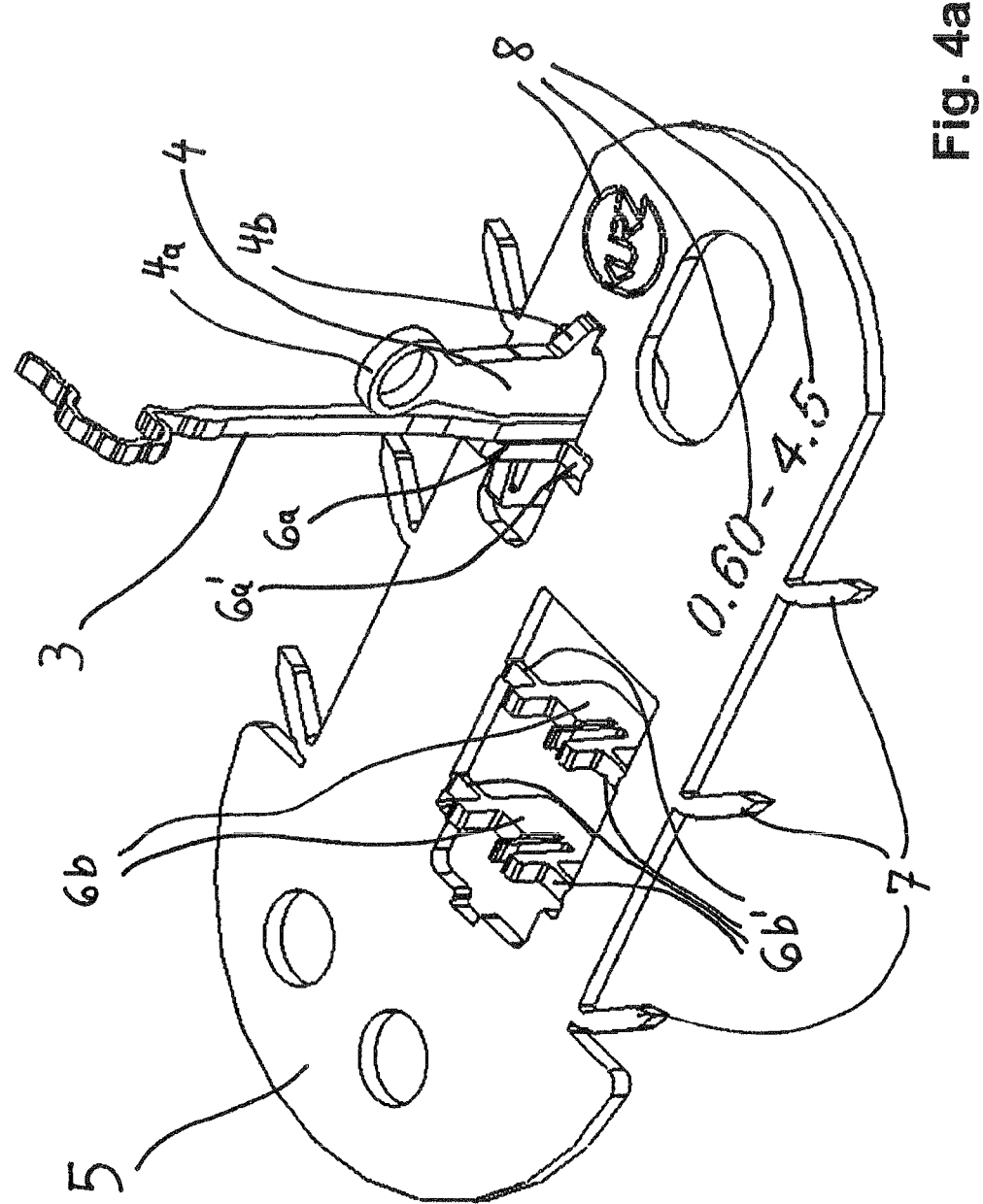
Figure 5A:
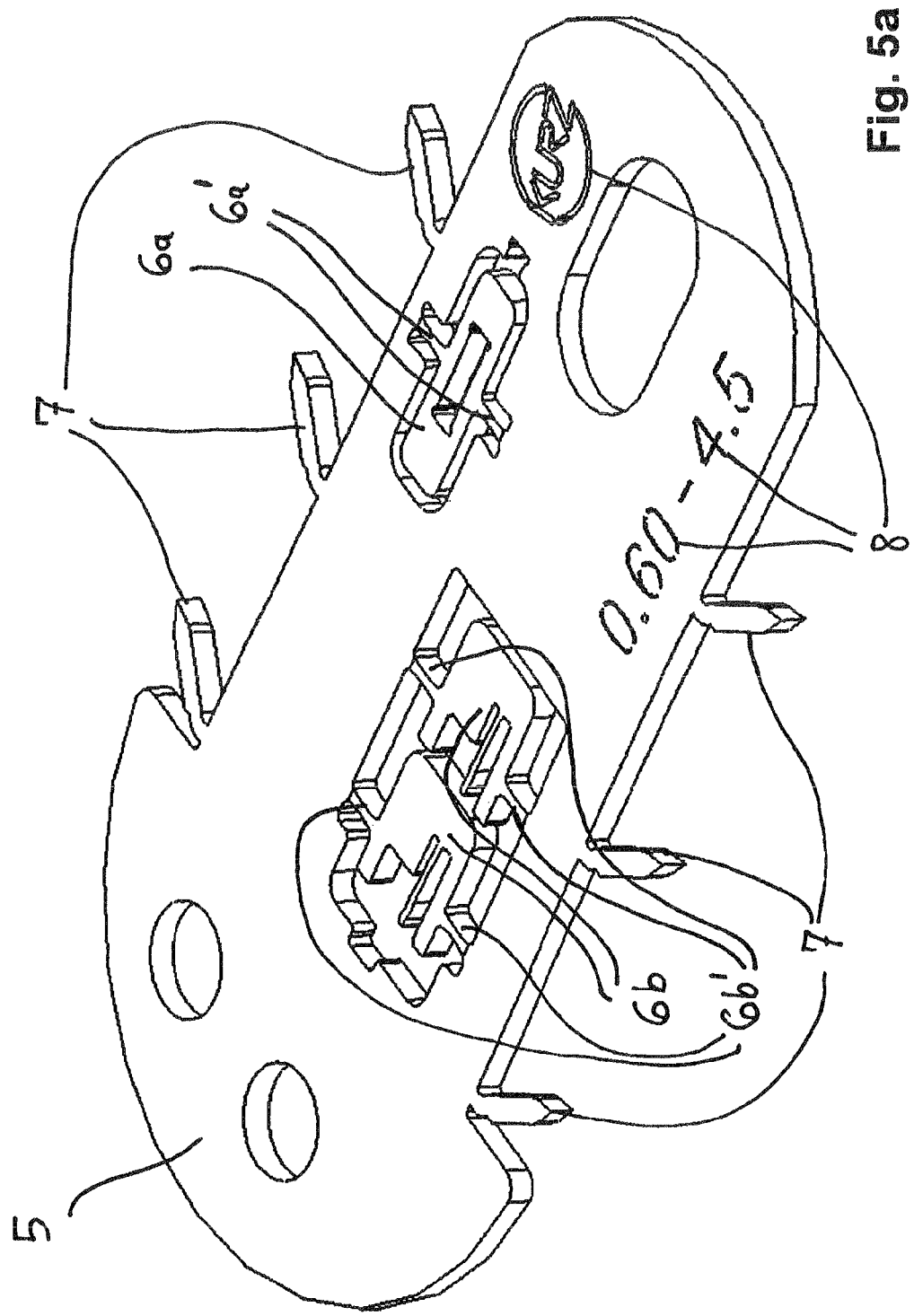
Figure 5B:
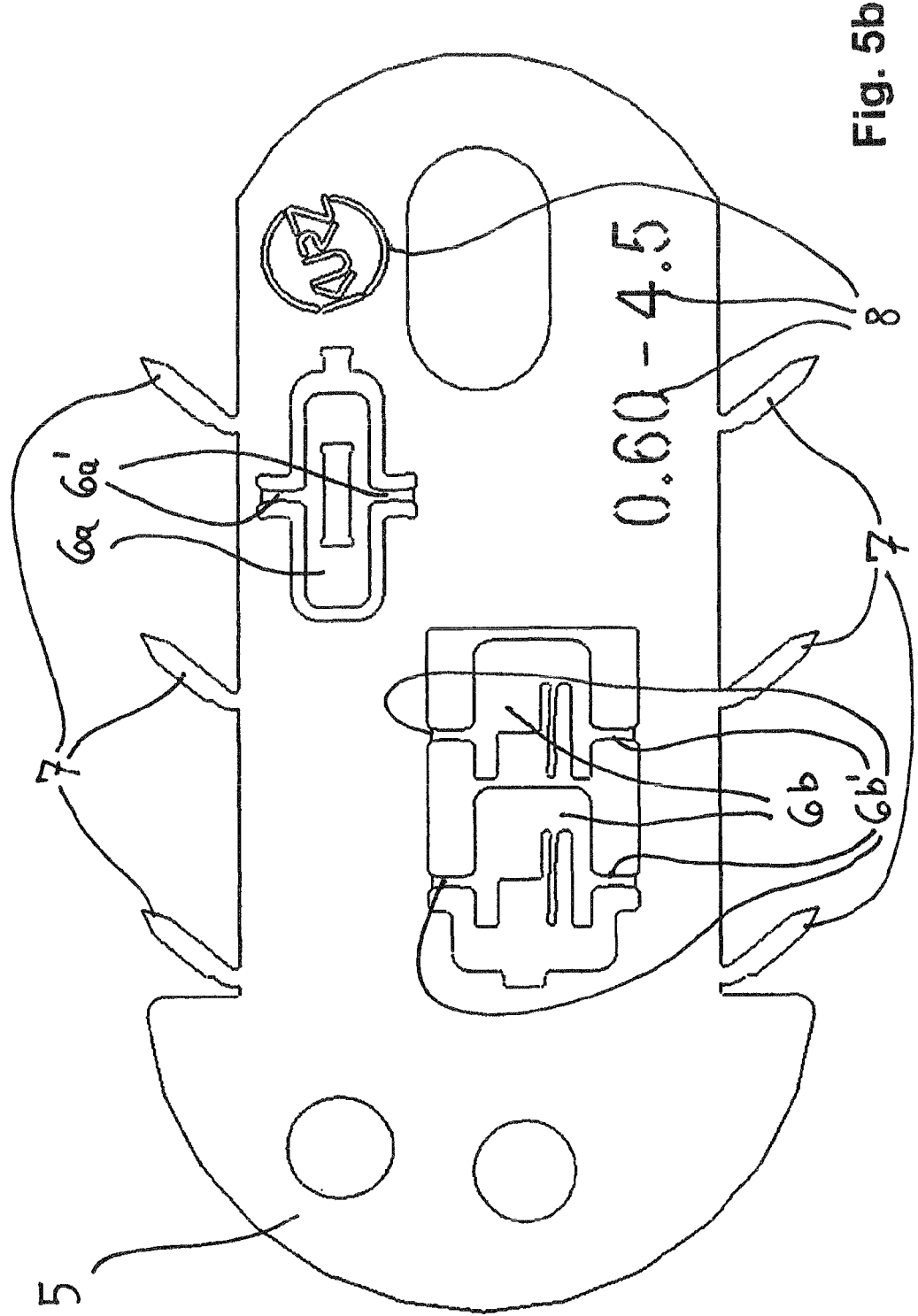
Figure 5C:
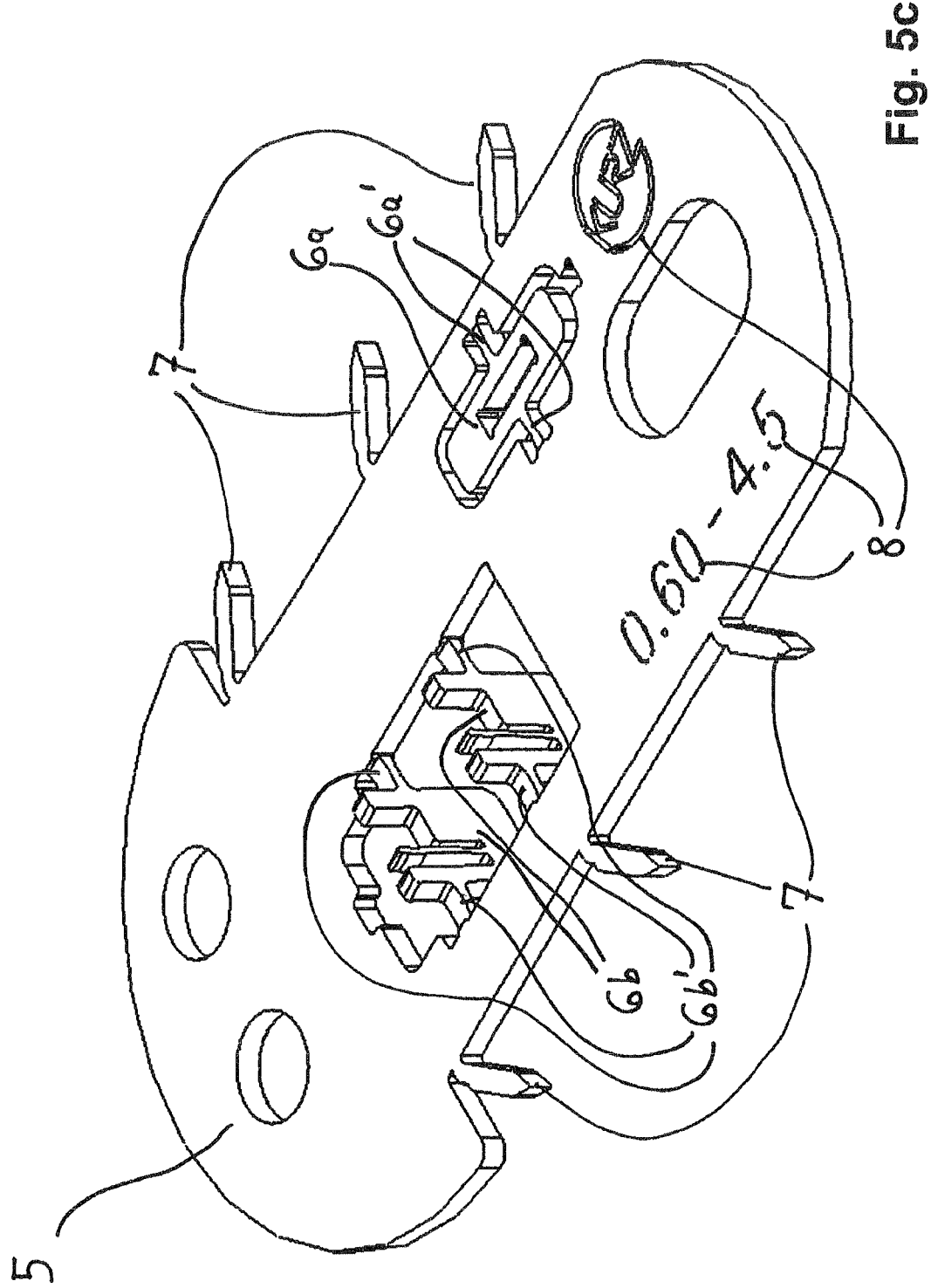
Figure 5D:
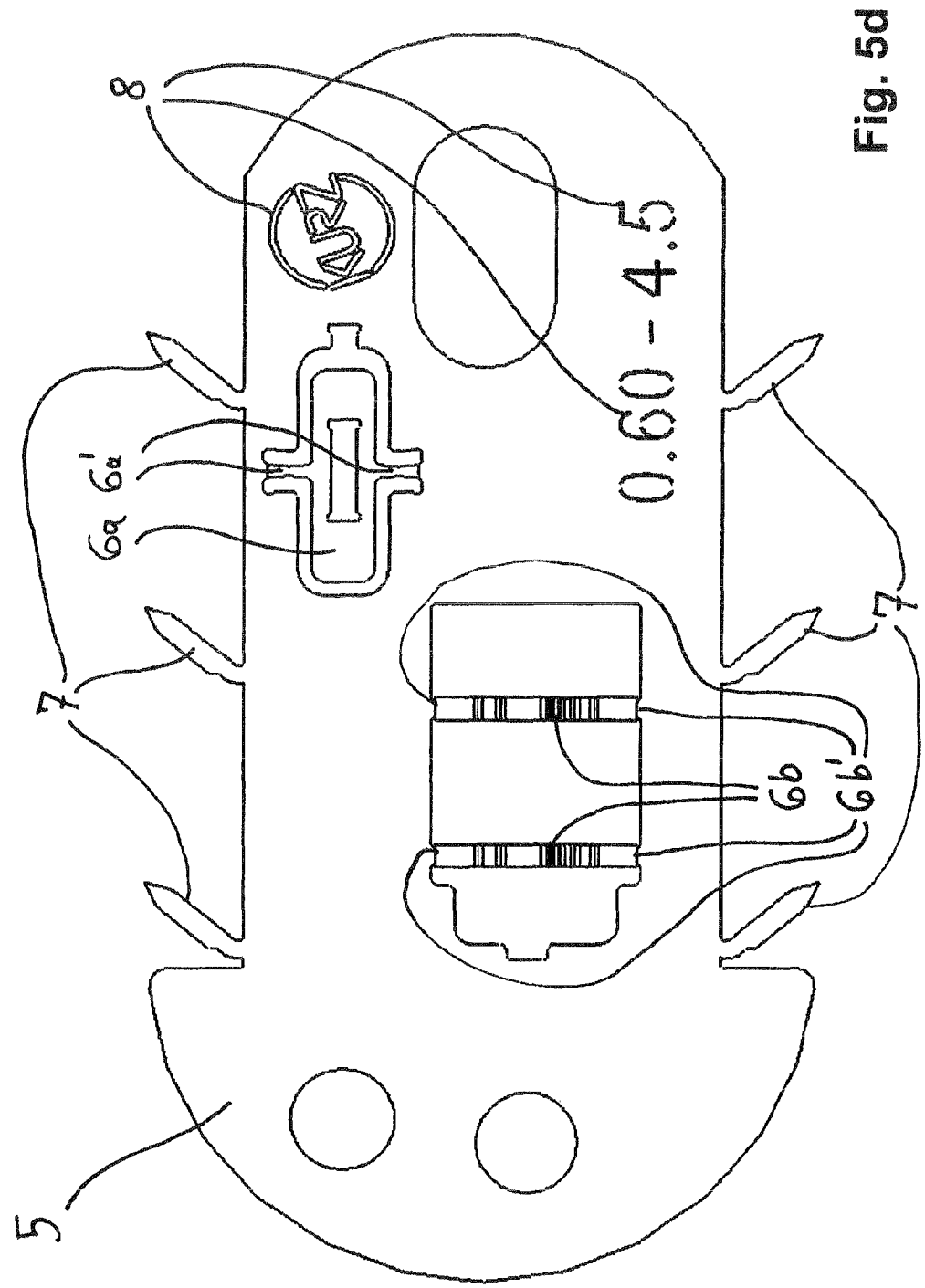

Shown are:

FIG. 1 an embodiment of the test device according to the invention that comprises, in addition to an associated ossicular prosthesis, a prosthesis mock-up accommodated on a holding device such that it can swivel in the region of a detent device, in a schematic spacial depiction at an angle from above;

FIG. 2a a detailed view of the embodiment depicted in FIG. 1, in the region of the detent device;

FIG. 2b a detailed view of the entire prosthesis mock-up depicted in FIG. 1 in a schematic spacial depiction at an angle from above, rotated by approximately 180° relative to FIG. 1;

FIGS. 3a-3e the embodiment depicted in FIG. 1, in a schematic horizontal projection
(a) from above,
(b) from below,
(c) of an end face I,
(d) of the opposite end face II, and
(e) of one longitudinal side III;

FIG. 4a the embodiment depicted in FIG. 1 in a schematic spacial depiction at an angle from above with the ossicular prosthesis removed, and with the prosthesis mock-up upright and locked in position with the holding device;

FIG. 4b is the same as FIG. 4a, but rotated by approximately 180° from the perspective of the opposite longitudinal side;

FIG. 5a the holding device of the embodiment depicted in FIG. 1 without the ossicular prosthesis and without the prosthesis mock-up, and with the detent device and a swivellable holder for the ossicular prosthesis, both in the unswivelled state;

FIG. 5b the holding device depicted in FIG. 5a in a schematic view from below;

FIG. 5c the holding device depicted in FIG. 5a comprising the swivellable holder for the ossicular prosthesis in the swivelled state; and FIG. 5d the holding device depicted in FIG. 5c in a schematic view from below.

The embodiment of the test device 1 according to the invention, which is depicted schematically in the figures of the drawing, comprising an ossicular prosthesis 2 for implantation in the middle ear, which has on one end thereof a first fastening element 2a for mechanical connection to the tympanic membrane or a component of the ossicular chain, and, on the other end thereof, a second fastening element 2b for mechanical connection to a further component of the ossicular chain or directly to the inner ear, and a connecting element 2c which connects the two fastening elements 2a, 2b in a sound-conducting manner, and wherein at least parts of ossicular prosthesis 2 are made of a material having memory effect and are subjected to shape-altering thermal treatment when the ossicular prosthesis 2 is implanted in the middle ear is characterized, according to the invention, in that the test device 1 comprises a device for determining an optimized power setting and/or energy application site for preparing parts of the ossicular prosthesis 2 to be subjected intraoperatively to thermal treatment, and in that the device contains a prosthesis mock-up 3 which matches the prosthesis 2, which is identical in design to the ossicular prosthesis 2 in terms of material, geometric shape, and manufacturing method, at least in the regions in which the associated prosthesis 2 will be subjected intraoperatively to thermal treatment.

In the embodiment of the invention depicted in the drawing, the ossicular prosthesis 2 of the test device 1 according to the invention and the associated prosthesis mock-up 3 are made of a material having memory effect, at least in the region of first fastening element 2a. In embodiments of the invention that are not depicted in the drawing, the prosthesis can also comprise a device for varying the length thereof, wherein, in that particular case, the prosthesis and the associated prosthesis mock-up are made of a material having memory effect, at least in the region of the device for varying the length. In embodiments of the test device according to the invention that are likewise not depicted in the drawing, the ossicular prosthesis and the associated prosthesis mock-up can be designed entirely identical to one another in terms of material and geometric shape.

In several embodiments of the invention, a nickel-titanium alloy, more particularly Nitinol, is used as the preferred material having memory effect.

In every representation of the prosthesis mock-up 3 shown in the drawing, a detent device 4 is provided, which is used to fix the prosthesis mock-up 3 in a processing position which is preferably upright, as shown in FIGS. 4a and 4b. Possible details of the detent device 4 are shown in enlarged depictions in FIGS. 2a and 2b, for example a tab-shaped operating element 4a or locking elements 4b, 4b' which, in the locked state, enclose a counter-holder, as shown clearly in FIG. 4b.

A feature that is also common to all of the embodiments of the test device 1 according to the invention shown in the drawing is that a holding device 5 is provided that can swivellably accommodate the prosthesis mock-up 3 is provided.

Said holding device 5 is preferably designed as a plate made of thin metal sheet and is shown from various sides in the drawing. FIGS. 1 and 3a to 3e show the plate comprising the installed ossicular prosthesis 2 and the prosthesis mock-up 3 in the lying-flat transport state; FIGS. 4a and 4b show the prosthesis mock-up 3 upright and locked in position after the prosthesis 2 has been removed; the prosthesis mock-up 3 and the prosthesis 2 are not shown in FIGS. 5a to 5d; FIGS. 5a and 5b especially show the state of the holding device 5 immediately after production thereof, and FIGS. 5c and 5d show the state shortly before installation of the ossicular prosthesis 2 on the holding device 5. Not shown are possible embodiments of the test device according to the invention, in which the holding device is designed such that it can accommodate only the prosthesis mock-up, but not the associated ossicular prosthesis.

The figures of the drawing show a particularly preferred embodiment of the invention, in which the holding device 5 comprises a suspending device 6a, which is connected to the plate and can be twisted by way of fine segments 6a', for suspending one end of the prosthesis mock-up 3, and further suspending devices 6b for the ossicular prosthesis 2. The latter are also twistably connected to the plate by way of small segments 6b'. As mentioned above, FIGS. 5c and 5d illustrate, in particular, the state of the holding device 5 shortly before installation of the ossicular prosthesis 2, wherein the suspending devices 6b for accommodating the prosthesis are rotated by way of the segments 6b' relative to the lying-flat state shown in FIGS. 5a and 5b by approximately 90° relative to the plate. In contrast, the prosthesis mock-up 3 is suspended in the unrotated state of the suspending device 6a for transporting the test device 1 to the operating surgeon, and is swivelled by approximately 90° relative to the plate and is locked into position—as shown clearly in FIGS. 4a and 4b—only in order to determine the optimal processing parameters of the ossicular prosthesis 2.

Furthermore, the holding device 5 comprises a device for ensuring safe transport, which has burr-shaped segments 7 extending laterally from the holding device 5. They are used to ensure that the holding device 5—comprising the installed ossicular prosthesis 2, which is relatively sensitive to mechanical damage, and the prosthesis mock-up 3 which is also installed—will not slip in an outer packaging of the test device 1 that is used during transport to the operating surgeon.

In the embodiment of the invention shown, the holding device 5 is optically coded or labelled. The coding or labelling 8 contains technical information on the ossicular prosthesis 2 and/or the associated prosthesis mock-up 3, and manufacturer's information. The coding can also include simple color coding. As an alternative or in addition thereto—in embodiments of the invention that are not depicted in the drawing— the ossicular prosthesis and/or the associated prosthesis mock-up can also be optically coded and/or labelled, wherein the coding or labelling also contains technical information on the ossicular prosthesis and/or prosthesis mock-up.

The technical information in the coding or labelling 8 contains, for example, a size classification of ossicular prosthesis 2 used, and a recommended starting value for the electrical power or luminous power which should be applied within the scope of a test handling of prosthesis mock-up 3 at the beginning of the determination of optimized processing parameters for the parts of ossicular prosthesis 2 to be subjected intraoperatively to thermal treatment.

The coding and/or labelling 8 is created most simply using laser treatment and/or anodizing. Likewise, the holding device 5 itself is preferably manufactured and machined further by laser-cutting the plate out of a larger sheet. In particular, the miniscule structures of the above-described elements of base plate 5, such as the suspending devices 6a and 6b, the associated twistable segments 6a' and 6b', and the burr-shaped segments 7 for ensuring safe transport can hardly be produced in any other manner.

In the embodiment shown of the test device 1 according to the invention, place-holder pins 9a, 9b are provided in the holding device 5 to hold open the first fastening element 2a of the ossicular prosthesis 2, as well as the corresponding section of the associated prosthesis mock-up 3, in a defined manner during transport to the operating surgeon; said place-holder pins 9a, 9b lock the thermally pretreated parts made of material having memory effect in the desired geometry, thereby ensuring that unwanted changes in shape are prevented even if warming occurs during transport.

The embodiment of the invention depicted in the figures of the drawing shows an ossicular prosthesis 2, in the case of which the first fastening element 2a is in the form of a clamp that can be clipped onto the limb of incus, for example, or onto another component of the ossicular chain. In this embodiment, second fastening element 2b is designed, on the end opposite the clamp, as a piston for use to couple ossicular prosthesis 2 directly to the inner ear.

In embodiments of the invention according to the invention that are not shown in the drawing, the fastening elements 1a, 2b of the ossicular prosthesis 2 can also be designed differently, for example, as a sleeve, loop or hook. The first fastening element 2a can be a top plate for placement against the tympanic membrane. In addition, the second fastening element 2b, for example, can be designed not as a piston but rather in the form of a clamp or piston for placement against the base of the stapes, or as a slotted bell for fastening the ossicular prosthesis 2 to the stapes.

In further embodiments of the invention that are not depicted in the drawing, a ball joint can be integrated into connecting element 2c in order to ensure a certain amount of post-operative flexibility of ossicular prosthesis 2 between the connection points thereof.

In addition, the drawing does not show embodiments in which the ossicular prosthesis 2 can be connected to an active vibration part of an active, partially implantable hearing aid.

The mass distribution of the individual parts of the ossicular prosthesis 2 can be calculated depending on a desired, specifiable frequency response of sound conduction in the middle ear such that it is possible to tune the sound propagation properties in an individualized manner.

The invention claimed is:

1. A test device (1) comprising an ossicular prosthesis (2) for implantation in the middle ear, which replaces or bridges at least one component or parts of a component of the human ossicular chain, wherein the ossicular prosthesis (2) includes, at one end thereof, a first fastening element (2a) for mechanical connection to the tympanic membrane or a component of the ossicular chain, and, at the other end thereof, includes a second fastening element (2b) for mechanical connection to a further component, or parts of a component, of the ossicular chain, or directly to the inner ear, and includes a connecting element (2c) that connects the two fastening elements (2a, 2b) in a sound-conducting manner, and wherein at least parts of the ossicular prosthesis (2) are made of a material having memory effect and are subjected to shape-altering thermal treatment when the ossicular prosthesis (2) is implanted in the middle ear, characterized in that the test device (1) comprises a device for determining an optimized power setting or an energy application site for preparing parts of the ossicular prosthesis (2) to be subjected intraoperatively to thermal treatment or both, wherein the device for determining contains a prosthesis mock-up (3), which matches the ossicular prosthesis (2) and is identical in design to the ossicular prosthesis (2) in terms of material, geometric shape, and manufacturing method, at least in the regions in which the ossicular prosthesis (2) will be subjected intraoperatively to thermal treatment.

2. The test device according to claim 1, characterized in that the ossicular prosthesis (2) comprises a device for varying the length thereof, and in that the ossicular prosthesis (2) and the prosthesis mock-up (3) are made of a material having memory effect at least in the region of the device for varying the length.

3. The test device according to claim 1, characterized in that the ossicular prosthesis (2) and the prosthesis mock-up (3) are made of a material having memory effect, at least in the region of the first fastening element (2a).

4. The test device according to claim 1, characterized in that the ossicular prosthesis (2) and the prosthesis mock-up (3) are designed entirely identical to one another in terms of material and geometric shape.

5. The test device according to claim 1, characterized in that the test device (1) contains a detent device (4), which is used to fix the prosthesis mock-up (1), at least in a processing position.

6. The test device according to claim 1, characterized in that a holding device (5) is provided to swivellably accommodate the prosthesis mock up (3).

7. The test device according to claim 6, characterized in that the holding device (5) is produced as a plate made of thin metal sheet and comprises a suspending device (6a), which is twistably connected to the plate, for suspending one end of the prosthesis mock-up (3).

8. The test device according to claim 6, characterized in that the holding device (5) comprises a device for ensuring safe transport, which comprises burr-shaped segments (7) extending laterally from the holding device (5).

9. The test device according to claim 6, characterized in that the holding device (5) accommodates the prosthesis mock-up (3).

10. The test device according to claim 6, characterized in that the holding device (5) is optically coded, labeled or both, and in that the coding or labeling (8) contains technical information regarding the ossicular prosthesis (2), the prosthesis mock-up (3), manufacturer's information or a combination thereof.

11. The test device according to claim 1, characterized in that one of the ossicular prosthesis (2), the associated prosthesis mock-up (3) and both are optically coded, labeled or both, and in that the coding or labeling (8) contains technical information regarding the ossicular prosthesis (2), the prosthesis mock-up (3) information or a combination thereof.

12. The test device according to claim 10, characterized in that the coding or labeling (8) is created using laser treatment, anodizing or both.

13. The test device according to claim 10, characterized in that the technical information of the coding or labeling (8) contains a recommended starting value for the optimized power setting or a luminous power setting to be used within the scope of a test handling of the prosthesis mock-up (3) at the beginning of the determination of optimized processing parameters for the parts of the ossicular prosthesis (2) to be subjected intraoperatively to thermal treatment.

14. The test device according to claim 1, characterized in that at least parts of the ossicular prosthesis (2) and the associated prosthesis mock-up (3) are made of a nickel-titanium alloy.

15. The test device according to claim 1, characterized in that the ossicular prosthesis (2) is connected to an active vibration part of an active, partially implantable hearing aid.

16. The test device according to claim 1, wherein the first fastening element (2a) is connected to a limb of incus or a manubrium of malleus.

17. The test device according to claim 14, wherein the nickel-titanium alloy is Nitinol.

18. A test device (1) comprising:

an ossicular prosthesis (2) for implantation in the middle ear, which replaces or bridges at least one component or parts of a component of the human ossicular chain, wherein the ossicular prosthesis (2) includes a first fastening element (2a) for mechanical connection to the tympanic membrane or a component of the ossicular chain at one end, a second fastening element (2b) for mechanical connection to a further component, or parts of a component of the ossicular chain or, directly to the inner ear at the other end and, a connecting element (2c) that connects the two fastening elements (2a, 2b) in a sound-conducting manner, and wherein at least parts of the ossicular prosthesis (2) are made of a material having memory effect and are subjected to shape-altering thermal treatment when the ossicular prosthesis (2) is implanted in the middle ear;

a device for determining an optimized power setting or an energy application site for preparing parts of the ossicular prosthesis (2) to be subjected intraoperatively to thermal treatment or both, and wherein the device for determining contains a prosthesis mock-up (3), which matches the ossicular prosthesis (2) and is identical in design to the ossicular prosthesis (2) in terms of material, geometric shape, and manufacturing method, at least in the regions in which the ossicular prosthesis (2) will be subjected intraoperatively to thermal treatment; and a holding device (5) is provided to swivellably accommodate the prosthesis mock-up (3) and is produced as a plate made of thin metal sheet and comprises a suspending device (6a), wherein the suspending device is twistably connected to the plate for suspending one end of the prosthesis mock-up (3).

19. A test device (1) comprising:

an ossicular prosthesis (2) for implantation in the middle ear, which replaces or bridges at least one component or parts of a component of the human ossicular chain, wherein the ossicular prosthesis (2) includes a first fastening element (2a) for mechanical connection to the tympanic membrane or a component of the ossicular chain at one end, a second fastening element (2b) for mechanical connection to a further component, or parts of a component of the ossicular chain or, directly to the inner ear at the other end and, a connecting element (2c) that connects the two fastening elements (2a, 2b) in a sound-conducting manner, and wherein at least parts of the ossicular prosthesis (2) are made of a material having memory effect and are subjected to shape-altering thermal treatment when the ossicular prosthesis (2) is implanted in the middle ear;

a device for determining an optimized power setting or an energy application site for preparing parts of the ossicular prosthesis (2) to be subjected intraoperatively to thermal treatment or both, and wherein the device for determining contains a prosthesis mock-up (3), which matches the ossicular prosthesis (2) and is identical in design to the ossicular prosthesis (2) in terms of material, geometric shape, and manufacturing method, at least in the regions in which the ossicular prosthesis (2) will be subjected intraoperatively to thermal treatment; and a holding device (5) is provided to swivellably accommodate the prosthesis mock-up (3) and is optically coded, labeled or both, wherein the coding or labeling (8) contains technical information regarding the ossicular prosthesis (2), the prosthesis mockup (3), manufacturer's information or a combination thereof and wherein the technical information of the coding or labeling (8) contains a recommended starting value for the optimized power setting or a luminous power setting to be used within the scope of a test handling of the prosthesis mock-up (3) at the beginning of the determination of optimized processing parameters for the parts of the ossicular prosthesis (2) to be subjected intraoperatively to thermal treatment.

* * * * *